US011213550B2

(12) United States Patent
Makino et al.

(10) Patent No.: US 11,213,550 B2
(45) Date of Patent: Jan. 4, 2022

(54) CELL PREPARATION FOR TREATING CARTILAGE TISSUE-RELATED DISORDER

(71) Applicant: NIPPON SHOKUBAI CO., LTD., Osaka (JP)

(72) Inventors: Tomomi Makino, Osaka (JP); Takuma Nakada, Osaka (JP); Masaaki Ii, Osaka (JP)

(73) Assignee: NIPPON SHOKUBAI CO., LTD., Osaka (JP)

(*) Notice: Subject to any disclaimer, the term of this patent is extended or adjusted under 35 U.S.C. 154(b) by 259 days.

(21) Appl. No.: 16/465,935

(22) PCT Filed: Dec. 4, 2017

(86) PCT No.: PCT/JP2017/043448
§ 371 (c)(1),
(2) Date: May 31, 2019

(87) PCT Pub. No.: WO2018/101481
PCT Pub. Date: Jun. 7, 2018

(65) Prior Publication Data
US 2019/0307807 A1 Oct. 10, 2019

(30) Foreign Application Priority Data

Dec. 2, 2016 (JP) .............................. JP2016-235286
Aug. 22, 2017 (JP) .............................. JP2017-159670

(51) Int. Cl.
*A61K 35/28* (2015.01)
*A61P 19/02* (2006.01)
*A61K 9/00* (2006.01)
*C12N 5/077* (2010.01)
*A61P 9/00* (2006.01)
*A61P 9/10* (2006.01)
*A61P 19/00* (2006.01)
*A61P 1/16* (2006.01)
*A61P 9/04* (2006.01)
*A61P 13/12* (2006.01)
*A61K 45/06* (2006.01)
*A61K 35/12* (2015.01)

(52) U.S. Cl.
CPC ............ *A61K 35/28* (2013.01); *A61K 9/0019* (2013.01); *A61P 1/16* (2018.01); *A61P 9/00* (2018.01); *A61P 9/04* (2018.01); *A61P 9/10* (2018.01); *A61P 13/12* (2018.01); *A61P 19/00* (2018.01); *A61P 19/02* (2018.01); *C12N 5/0653* (2013.01); *A61K 45/06* (2013.01); *A61K 2035/124* (2013.01)

(58) Field of Classification Search
None
See application file for complete search history.

(56) References Cited

U.S. PATENT DOCUMENTS

| 2016/0367601 A1* | 12/2016 | Lee ........................ A61K 35/32 |
| 2017/0009208 A1* | 1/2017 | Poon .................... C12N 5/0663 |
| 2017/0175078 A1* | 6/2017 | Makino .............. C08G 73/1039 |
| 2018/0042966 A1 | 2/2018 | Hung |

FOREIGN PATENT DOCUMENTS

| JP | 2005080599 A | 3/2005 |
| JP | 2009213716 A | 9/2009 |
| JP | 2011041472 A | 3/2011 |
| JP | 2013006959 A | 1/2013 |
| JP | 2015 213498 | * 12/2015 |
| JP | 2015213498 A | 12/2015 |
| JP | 2016-054734 A | 4/2016 |
| JP | 2016054724 A | 4/2016 |
| JP | 2016140308 A | 8/2016 |
| JP | 2016171778 A | 9/2016 |
| WO | 2015163043 A1 | 10/2015 |
| WO | 2016131430 A1 | 8/2016 |

OTHER PUBLICATIONS

Pittenger et al, 1999, Science. 284:143-7.
Huang, Guo-Shiang et al., Spheroid formation of mesenchymalstem sells on chitosan and chitosan-hyaluronan membranes, Biometals, Jul. 16, 2011, vol. 32, p. 6929-6956.
Zhang, Kunxi et al., In-situ birthe of MSCs multicellular spheroids in poly . . . Aug. 20, 2015, vol. 71, p. 24-34.
Murata, Daiki, et al., J Orthop Res, Mar. 18, 2015, vol. 10, No. 35, p. 1-12.
EPO, Office Action for the corresponding European Patent Application No. 17 877 131.7, dated Mar. 5, 2021.
Zoe Cesarz et al., "Spheroid Culture of Mesenchymal Stem Cells," Stem Cells International, Jan. 1, 2016, pp. 1-11, vol. 2016.
KIPO, Office Action for the corresponding Korean Patent Application No. 10-2019-7014108, dated Dec. 24, 2020, with English translation.
EPO, Extended European Search Report for the corresponding European Patent Application No. 17877131.7, dated Apr. 24, 2020.
JPO, Notice of Reason for Refusal for the corresponding Japanese Patent Application No. 2018-554284, dated Apr. 14, 2020, with English translation.
Hee Hun Yoon, et al., "Enhanced Cartilage Formation via Three-Dimensional Cell Engineering of Human Adipose-Derived Stem Cells," Tissue Engineering, Sep. 10, 2012, pp. 1949-1956, vol. 18, Nos. 19 and 20.
JPO, Notice of Reason for Refusal for the corresponding Japanese Patent Application No. 2018-554284, dated Nov. 24, 2020, with English translation.

(Continued)

*Primary Examiner* — Ralph J Gitomer
(74) *Attorney, Agent, or Firm* — Lucas & Mercanti, LLP

(57) ABSTRACT

To provide a spheroid-containing cell preparation exhibiting a high therapeutic effect for a cartilage tissue-related disorder as a treatment target.

A prophylactic or therapeutic agent for a cartilage tissue-related disorder contains, as an effective ingredient, a spheroid including cultured mesenchymal stem cells.

5 Claims, 3 Drawing Sheets

(56) References Cited

OTHER PUBLICATIONS

Jorge M. Santos, et al., "Three-Dimentional Spheroid Cell Culture of Umbilical Cord Tissue-Derived Mesenchymal Stromal Cells Leads to Enhanced Prarciine Induction of Wound Healing," Stem Cell Research & Therapy, 2015, pp. 1-19, vol. 6, No. 90.
S. P. Camoes, et al., "Human Neonatal Mesenchymal Stem Cell Spheroids-Conditioned Medium Accelerates Skin Regeneration," Toxicology Letters, item P22-044, pp. 376-377, 2015, vol. 238S.
Xuan Zhang, et al., "3D Spheroid Culture Enhances the Expression of Antifibrotic Factors in Human Adipose-Derived MSCs anf Improves Their Therapeutic Effects on Hepatic Fibrosis," Stem Cells International, Article ID 4626073, pp. 1-8, 2016, vol. 2016.
In-Su Park et al., "Enhance Angiogenic Effect of Adipose-Derived Stomal Cell Spheroid with Low-Level Light Therapy in Hind Limb Ischemia Mice," Biomaterials, pp. 9280-9289, 2014, vol. 35.
KIPO, Office Action for the corresponding Korean patent application No. 10-2019-7014108, dated May 27, 2020, with English translation.
JPO, Office Action for the corresponding Japanese Patent Application No. 2018-554284, dated Apr. 27, 2021, with English translation.
KIPO, Office Action for the corresponding Korean Patent Application No. 10-2019-7014108, dated Apr. 21, 2021, with English translation.
KIPO, Office Action for the corresponding Korean Patent Application No. 10-2021-7023083, dated Sep. 8, 2021, with English translation.

\* cited by examiner

FIG. 1
(a)
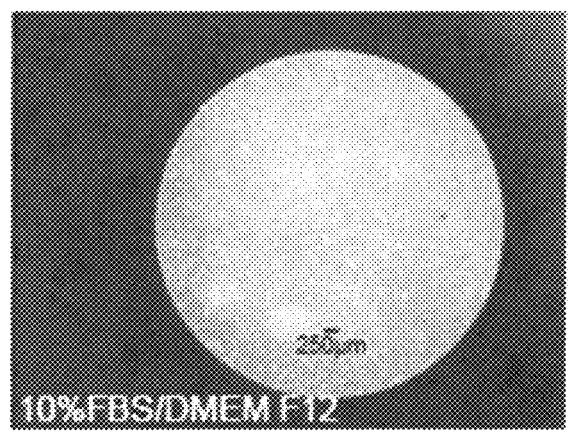
(b)
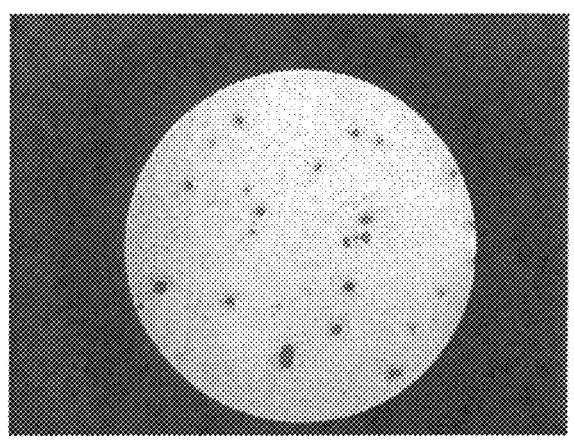
FIG. 2

FIG. 3

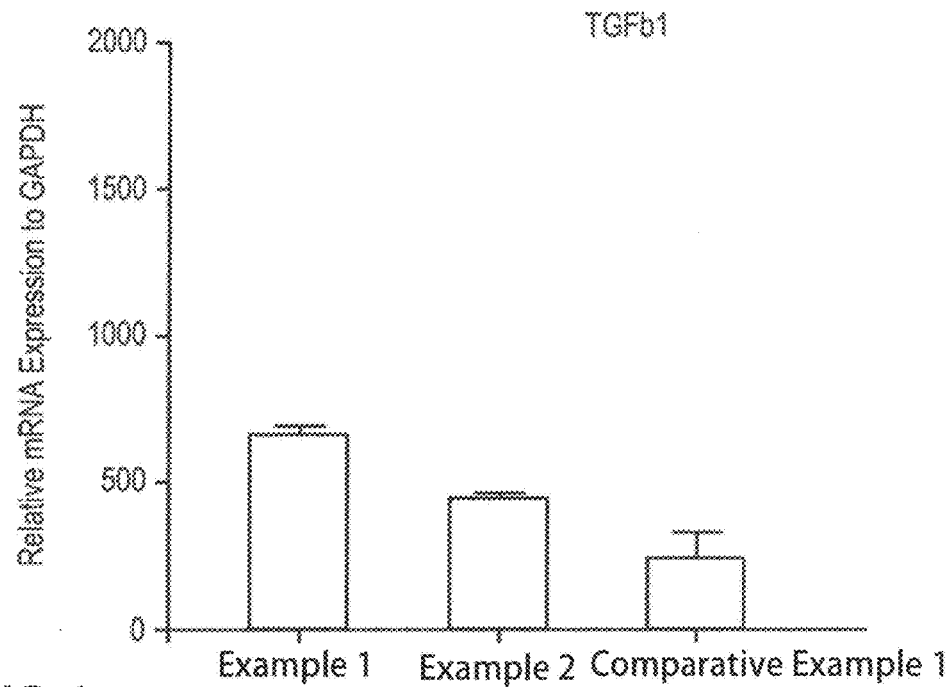

FIG. 4
METHOD FOR SEMI-QUANTITATIVE SCORING EVALUATION OF LEVEL OF HISTOLOGICAL DAMAGE IN JOINT

SCORING BASED ON HISTOPATHOLOGICAL FINDING IN CARTILAGE LAYER
  0: NORMAL
  0.5: REDUCED AREA OF SAFRANIN O STAINING (TISSUE FORMATION IS MAINTAINED)
  1: DEPOSITION OF SMALL AMOUNT OF FIBRIN (NO REDUCTION IN CARTILAGE TISSUES)
  2: CRACK (LIMITED TO CARTILAGE SURFACE LAYER + SLIGHT REDUCTION IN THIN SURFACE FILM)
  3: CRACK + EROSION (REACHING CALCIFIED CARTILAGE LAYER + 25% OR LESS OF PERIPHERAL LENGTH)
  4: CRACK + EROSION (REACHING CALCIFIED CARTILAGE LAYER + 25 TO 50% OF PERIPHERAL LENGTH)
  5: CRACK + EROSION (REACHING CALCIFIED CARTILAGE LAYER + 50 TO 75% OF PERIPHERAL LENGTH)
  6: CRACK + EROSION (REACHING CALCIFIED CARTILAGE LAYER + 75% OR MORE OF PERIPHERAL LENGTH)

REFERENCE : Osteoarthritis and Cartilage 18 (2010) S17-S23

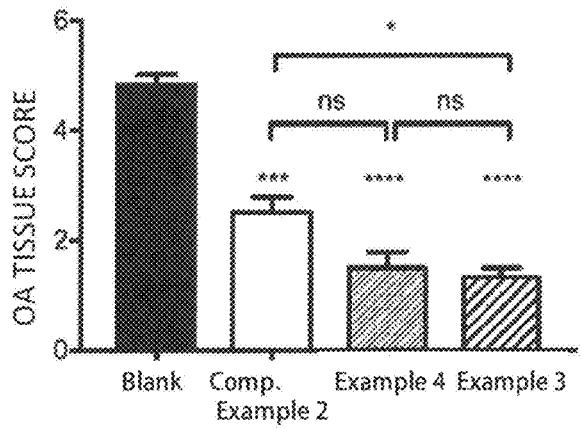

IMAGE OF JOINT CARTILAGE TISSUES (SAFRANIN O STAINING)

╱ : CARTILAGE LAYER OF HEAD OF TIBIA

RED : SAFRANIN O-POSITIVE CARTILAGE BASE

CELL PREPARATION FOR TREATING CARTILAGE TISSUE-RELATED DISORDER

CROSS REFERENCE TO RELATED APPLICATION

This Application is a 371 of PCT/JP2017/043448 filed on Dec. 4, 2017, which, in turn, claimed the priority of Japanese Patent Application No. 2016-235286 filed on Dec. 2, 2016, and Japanese Patent Application No. 2017-159670 filed on Aug. 22, 2017, all applications are incorporated herein by reference.

TECHNICAL FIELD

The present invention relates to a cell preparation. More specifically, the present invention relates to a prophylactic or therapeutic agent for a specific disorder containing, as an effective ingredient, a predetermined cell culture product.

BACKGROUND ART

Mesenchymal stem cells (MSCs) have an excellent self-regeneration property and pluripotency. Due to this reason, the mesenchymal stem cells are expected to be used as a potential cell source of a cell preparation to be employed for a cell treatment (Non Patent Literature 1).

When those mesenchymal stem cells are used as a cell preparation, using them in the form of a spheroid (cell mass; cell aggregate), in which cultured cells form a three-dimensional network, is preferable from the viewpoint of enhancing the effect of healing a lesion caused by disorder.

Among the cell preparations containing spheroid as an effective ingredient, a cell preparation exhibiting a high therapeutic effect for a cartilage tissue-related disorder as a treatment target is not known yet.

CITATION LIST

Non Patent Literature

Non Patent Literature 1: Pittenger et al., 1999, Science. 284:143-7

SUMMARY OF INVENTION

Technical Problem

Accordingly, an object of the present invention is to provide a spheroid-containing cell preparation exhibiting a high therapeutic effect for a cartilage tissue-related disorder as a treatment target.

Solution to Problem

To solve the aforementioned problem, the inventors of the present invention conducted intensive studies. As a result, it was surprisingly found that a cell preparation which contains, as an effective ingredient, a spheroid including cultured mesenchymal stem cells exhibits a high therapeutic effect for a cartilage tissue-related disorder, and the present invention is completed accordingly.

Namely, the present invention relates to a prophylactic or therapeutic agent for a cartilage tissue-related disorder containing, as an effective ingredient, a spheroid including cultured mesenchymal stem cells.

Advantageous Effect of the Invention

According to the present invention, a spheroid-containing cell preparation exhibiting a high therapeutic effect for a cartilage tissue-related disorder as a treatment target is provided.

BRIEF DESCRIPTION OF DRAWINGS

FIG. 1 is a photograph showing the observation image of the proceeding of adherent culture of mesenchymal stem cells in Example 1, in which the observation is made by using an optical microscope. FIG. 1(a) represents an observation image on Day 1 of the culture, and FIG. 1(b) represents an observation image on Day 3 of the culture.

FIG. 2 is a photograph showing the observation image of the proceeding of suspension culture of mesenchymal stem cells in Example 2, in which the observation is made by using an optical microscope.

FIG. 3 is a graph showing the result of measuring mRNA expression amount of human TGFβ1 gene (factor for causing cartilage differentiation) in cultured mesenchymal stem cells in Example 1, Example 2, and Comparative Example 1.

FIG. 4 is a graph showing the result of semi-quantitative scoring evaluation of level of histological damage in joint in a model mouse with arthrosis deformans of knee joint, which has been administered with planar cultured mesenchymal stem cells obtained from Comparative Example 2 or mesenchymal stem cell spheroid obtained from Example 3 and Example 4 (lower score indicates less damage in joint).

DESCRIPTION OF EMBODIMENTS

Figure 5:
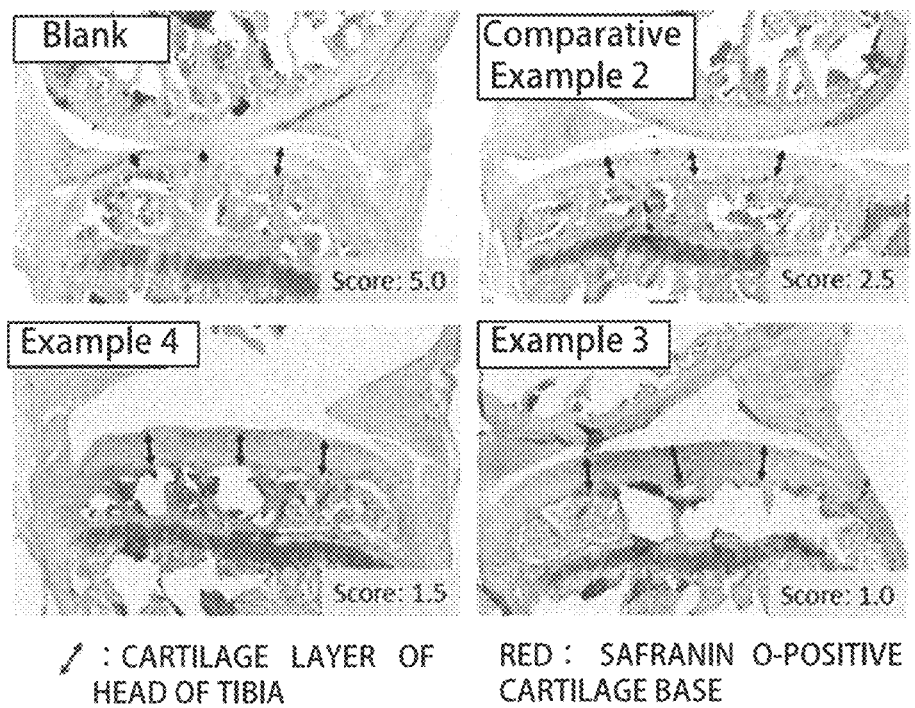
FIG. 5 is microscopic image showing the result of performing safranin O staining for joint tissues of a model mouse with arthrosis deformans of knee joint, which has been administered with planar cultured mesenchymal stem cells obtained from Comparative Example 2 or mesenchymal stem cell spheroid obtained from Example 3 and Example 4 (lower score indicates less damage in joint).

An aspect of the present invention is a prophylactic or therapeutic agent for a cartilage tissue-related disorder containing, as an effective ingredient, a spheroid including cultured mesenchymal stem cells.

Hereinbelow, embodiments of the present invention are explained. Furthermore, the present invention is not limited to the following embodiments. As described herein, the expression "X to Y" representing a range means "X or more to Y or less". In addition, unless particularly described otherwise, operations and measurements of physical property or the like are carried out at conditions of room temperature (20 to 25° C.)/relative humidity of 40 to 50% RH.

<Effective Ingredient (Spheroid)>

The prophylactic or therapeutic agent for a cartilage tissue-related disorder according to this aspect contains, as an effective ingredient, a spheroid including mesenchymal stem cells. As described herein, the terms "spheroid" means an aggregate of cells (cell mass), and it is intended that a three-dimensional cell aggregate is also encompassed by this concept. Furthermore, although the size of spheroid is not particularly limited, diameter of the spheroid is preferably 1 to 500 μm, and preferably 10 to 300 μm, for example. Herein, diameter of the spheroid can be measured by a common method (measurement of particle size distribution).

(Mesenchymal Stem Cells (MSCs))

The spheroid as an effective ingredient according to this aspect is characterized in that cultured mesenchymal stem cells are included therein. The MSCs provided for culture are not particularly limited as long as they are undifferentiated mesenchymal cells, and those collected from bone marrow, bone membrane, adipose tissues, peripheral blood, or the like of mammals by a common method can be used. Furthermore, after the collection, selection of undifferentiated MSCs can be made in view of the presence or absence of adhesion on plastics or the like. Herein, from the viewpoint of easy obtainability and high proliferation property, the mesenchymal stem cells derived from adipose tissues are preferably used as MSCs. Furthermore, as for the MSCs, it is preferable to use MSCs derived from a mammal which belongs to the same species as the subject for administering the prophylactic or therapeutic agent of the present invention, and MSCs derived from a mammal of the same species other than the subject for administration, or own MSCs of the subject for administration (autologous cells) can be used. The biospecies from which those cells are derived are not particularly limited, either, and various cells derived from human and non-human mammal can be used. Examples of the biospecies from which the cells are derived include primates such as human, red-haired monkey, green monkey, crab-eating macaque, chimpanzee, tamarin, marmoset, and the like, rodents such as mouse, rat, hamster, guinea pig, and the like, dog, cat, rabbit, pig, cow, goat, sheep, horse, and the like. Furthermore, as for the MSCs that are provided for culture, MSCs of passage 1 to 10 can be used when the cells obtained by proliferation of MSCs to 70 to 90% confluency (preferably 80% confluency) are taken as passage zero.

(Culture Conditions)

The spheroid as an effective ingredient according to the present aspect is characterized in that cultured mesenchymal stem cells are included therein. Culture conditions for obtaining the "cultured mesenchymal stem cells" to be included in the spheroid are not particularly limited, either, and it is possible for a person skilled in the art to suitably select the conditions allowing culture of mesenchymal stem cells (MSCs).

Specifically, there is suspension culture and adherent culture as the form of culturing mesenchymal stem cells. Between them, the culture is preferably "adherent culture" in the present invention. The "adherent culture" is a concept against "suspension culture", and it means that cells to be cultured or a spheroid including the cells are cultured by adhering them on a surface of a base for cell culture. The expression "cells to be cultured or a spheroid including the cells are adhered on a surface of a base for culture" during culture means a state in which the cells or spheroid are adhered, via a cell-substrate adhesion molecule included in ECM (extracellular matrix) or the like, on a surface of a base for culture, and it indicates a state in which suspension of the cells or spheroid in a medium does not occur even when the medium is gently shaken. On the other hand, the "suspension culture" means culture without having adhesion of the cells to be cultured or spheroid including the cells on a surface of a base for culture. The expression "cells to be cultured or spheroid including the cells do not adhere on a surface of a base for culture" during culture means a state in which the cells or spheroid are not adhered on a bottom surface of a base for culture via a cell-substrate adhesion molecule included in ECM or the like, and it indicates a state in which, even when the cells or spheroid are in contact with a bottom surface of a base for culture, for example, they become suspended in the medium as a result of gentle shaking of the medium or they remain precipitated without showing adhesion, or the like. Quantitatively speaking, the determination is made as follows in the present specification: when the medium is completely removed from a medium containing cells or a spheroid in a culture vessel and the medium is added again to the same vessel at a rate of 0.1 mL/sec thereafter, if the cells or spheroid are detached and suspended from the bottom surface or the cells or spheroid travel by 500 µm or more, it is determined that the cells or spheroid are "suspended" (that is, the cells or spheroid do not adhere on a surface of a base for culture).

The medium used for cell culture may be suitably selected depending on cells. Type of the medium is not particularly limited, but, for example, any basic medium for cell culture or differentiation medium, medium exclusive for primary cell culture or the like can be used. Specific examples thereof include Eagle's minimum essential medium (EMEM), Dulbecco's modified Eagle medium (DMEM), α-MEM, Glasgow MEM (GMEM), IMDM, RPMI1640, Ham F-12, MCDB medium, William medium E, Hepatocyte thaw medium, medium exclusive for MSC, a mixture medium of those, and the like. However, the medium is not limited to them, and any medium can be used as long as it contains a component required for proliferation or differentiation of cells. Furthermore, it is also possible to use a medium added with blood serum, various growth factors, factors for inducing differentiation, antibiotics, hormones, amino acids, sugars, salts, or the like. The culture temperature is not particularly limited, either. However, the culture is generally carried out at 25 to 40° C. or so.

Time for subjecting to culture is not particularly limited, either, and it can be suitably set by considering the cell proliferation rate, target size of spheroid, or the like. Herein, time for culture is preferably 4 hours to 30 days (4 to 720 hours). It is more preferably 1 to 14 days (24 to 336 hours), and even more preferably 1 to 7 days (24 to 168 hours). Namely, it is preferable to use, as an effective ingredient, the spheroid obtained by culturing, from start of the culture, for a time period within that range.

When the culture of mesenchymal stem cells (MSCs) is adherent culture, specific constitutions of the base for cell culture are not particularly limited, and all conventionally known bases can be suitably used as long as they allow the culture of mesenchymal stem cells (MSCs).

(Base for Cell Culture)

As for the material of a base for cell culture, a resin or the like can be exemplified. However, from the viewpoint that it is not a material derived from a living organism, the base for cell culture preferably contains a resin. The resin is not particularly limited as long as it is a resin with high biocompatibility that can be used as a base for cell culture. For example, as the resin contained in a base for cell culture, a fluororesin, a polyimide resin (for example, fluorine-containing polyimide resin), polysulfone, polyether sulfone, polydimethyl siloxane, or the like, or a blend thereof can be exemplified. Furthermore, from the viewpoint that the material has high strength, a polyimide resin is preferably used. Namely, according to one preferred embodiment of the present invention, the base for cell culture contains a polyimide resin. As for the polyimide resin, a polyimide resin containing the constitutional unit that is represented by the following formula (I) can be exemplified. Furthermore, from the viewpoint of having favorable forming of a spheroid, a resin having fluorine atom in the molecule is preferable, and fluorine-containing polyimide (fluorine-containing polyimide resin) is more preferable. The polyimide resin used in the present invention is typically obtained by imidation of polyamide acid, which is obtained by polymerizing acid dianhydride and diamine, at least one kind for each. The polyimide resin may also include the polyamide acid in part of the chemical structure. With regard to a method for producing the polyimide resin, the production may be made by a known technique. For example, a two-stage synthetic method can be used. The two-stage method for synthesizing polyimide resin is a method in which polyamide acid is synthesized as a precursor and the polyamide acid is converted to polyimide acid. The polyamide acid as a precursor may be also a polyamide acid derivative. Examples of the polyamide acid derivative include polyamide acid salt, polyamide acid alkyl ester, polyamide acid amide, polyamide acid derivative from bismethylidene pyromellitimide, polyamide acid silyl ester, polyamide acid isoimide, and the like. Examples of the polyimide include polyimide consisting of acid anhydride such as pyromellitic acid dianhydride, biphenyl tetracarboxylic acid dianhydride, benzophenone tetracarboxylic acid dianhydride, and the like and diamine such as oxydiamine, paraphenylene diamine, metaphenylene diamine, benzophenone diamine, and the like. Examples of the resin having fluorine atom include a fluorine-containing polyimide resin which contains a constitutional unit represented by the following formula (I), for example, 4,4'-hexafluoroisopropylidene diphthalic acid anhydride (6FDA)/1,4-bis(aminophenoxy)benzene (TPEQ) copolymer, 6FDA/4,4'-oxydiphthalic acid anhydride (ODPA)/TPEQ copolymer, 4,4'-(4,4'-isopropylidenediphenoxy)diphthalic acid (BPADA)/2,2-bis[4-(4-aminophenoxy)phenyl] hexafluoropropane (HFBAPP), 6FDA/2,2-bis(4-(4-aminophenoxy)phenyl)propane (BAPP) copolymer or the like; an ethylene-tetrafluoroethylene copolymer; and the like.

[Chemical formula 1]

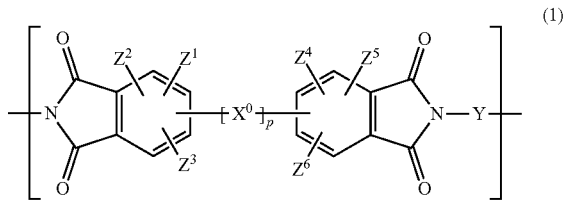

(1)

In the above formula (I), $X^0$ represents any one of an oxygen atom, a sulfur atom, and a divalent organic group; Y represents a divalent organic group; $Z^1$, $Z^2$, $Z^3$, $Z^4$, $Z^5$, and $Z^6$ each independently represent any one of a hydrogen atom, a fluorine atom, a chlorine atom, a bromine atom, and an iodine atom, and p is 0 or 1. Furthermore, in the polyimide resin, the chemical structure represented by the formula (I) may be the same or different from each other for each constitutional unit of the resin. At least one of $X^0$, Y, $Z^1$, $Z^2$, $Z^3$, $Z^4$, $Z^5$, and $Z^6$ preferably contains at least one fluorine atom.

In the above formula (I), in a case in which p=0, $X^0$ may not be present (in other words, benzene rings at the left and right sides are directly bonded to each other). On the other hand, in a case in which p=1, the benzene rings at the left and right sides are bonded via $X^0$.

Specific examples of the divalent organic group represented by $X^0$ include an alkylene group, an arylene group, an aryleneoxy group, an arylenethio group, and the like. Among them, an alkylene group, an aryleneoxy group, and an arylenethio group are preferable, an alkylene group and an aryleneoxy group are more preferable, and they may be substituted with the fluorine atom. Carbon atom number of the alkylene group is 1 to 12, for example. It is preferably 1 to 6.

As for the alkylene group substituted with the fluorine atom as an example of $X^0$, —$C(CF_3)_2$—, —$C(CF_3)_2$—C$(CF_3)_2$—, and the like can be exemplified. Among the aforementioned alkylene groups as an example of $X^0$, —$C(CF_3)_2$— is preferable.

As for the arylene group as an example of $X^0$, the followings can be exemplified, for example.

[Chemical formula 2]

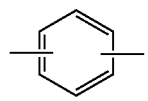

a-1

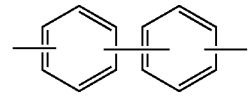

a-2

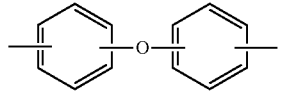

a-3

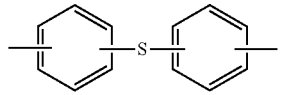

a-4

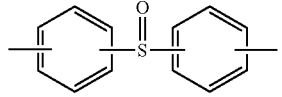

a-5

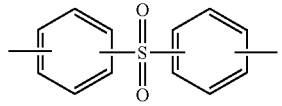

a-6

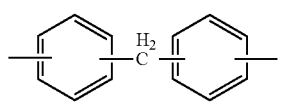

a-7

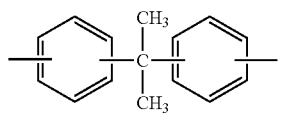

a-8

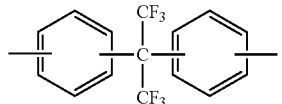

a-9

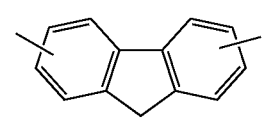

a-10

As for the aryleneoxy group as an example of $X^0$, the followings can be exemplified, for example.

[Chemical formula 3]

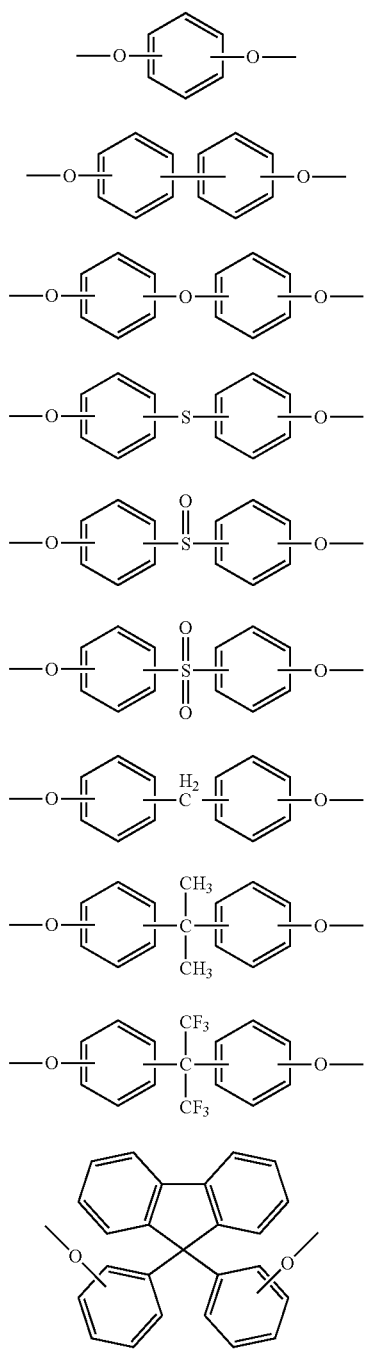

As for the arylenethio group as an example of $X^0$, the followings can be exemplified, for example.

[Chemical formula 4]

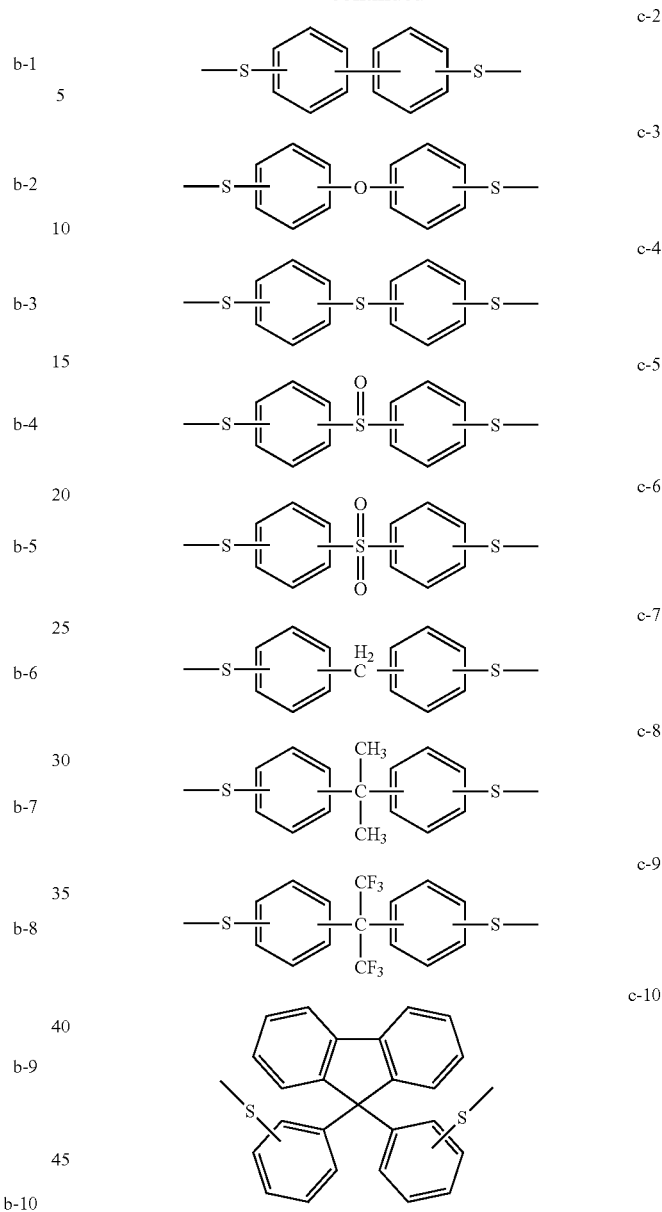

From the viewpoint that even the cells with reduced proliferation activity can favorably form a spheroid on a base, the divalent organic group represented by $X^0$ is preferably selected from the group consisting of above b-2 to b-10 and c-2 to c-10. It is more preferably selected from the group consisting of above b-7 to b-9 and c-7 to c-9, and it is even more preferably the structure represented by b-8. Furthermore, the divalent organic group represented by $X^0$ is preferably —C(CF$_3$)$_2$— similar to above.

The aforementioned arylene group, aryleneoxy group, and arylenethio group as an example of $X^0$ may be, each independently, substituted with a group selected from the group consisting of a halogen atom (for example, fluorine atom, chlorine atom, bromine atom, or iodine atom, preferably fluorine atom or chlorine atom, and more preferably fluorine atom), a methyl group, and a trifluoromethyl group. Those substituent groups may be present in plurality, and, in that case, type of the substituent may be the same or different from each other. The suitable substituent for substitution on the arylene group, aryleneoxy group, and arylenethio group is a fluorine atom and/or a trifluoromethyl group, and it is suitably a fluorine atom. When a fluorine atom is not included in Y, the arylene group, aryleneoxy group, and arylenethio group are preferably substituted with at least one fluorine atom.

In the above formula (I), as the divalent organic group represented by Y, a divalent organic group having an aromatic ring can be mentioned, for example, although it is not particularly limited thereto. Specifically, a group consisting of one benzene ring, and a group in which two or more benzene rings are directly bonded to each other or bonded via a carbon atom (that is, single bond or alkylene group), an oxygen atom, or sulfur atom can be mentioned. Specifically, the following groups can be exemplified.

[Chemical formula 5]

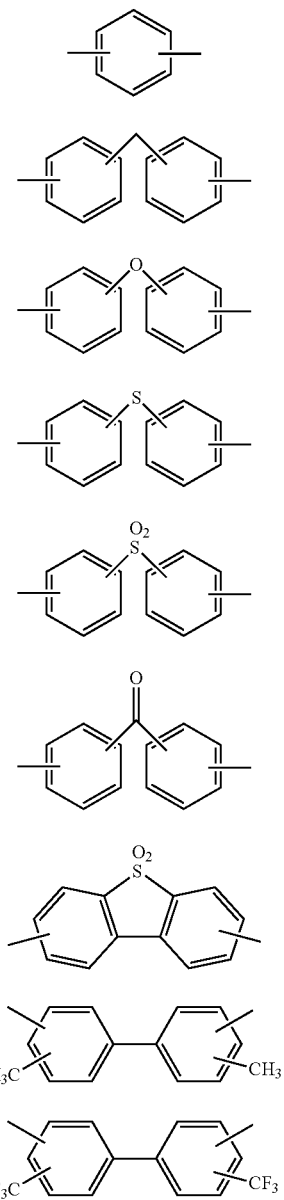

[Chemical formula 6]

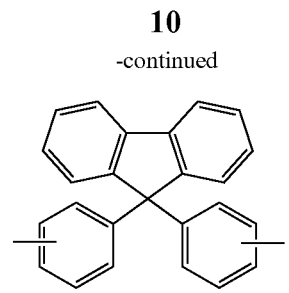

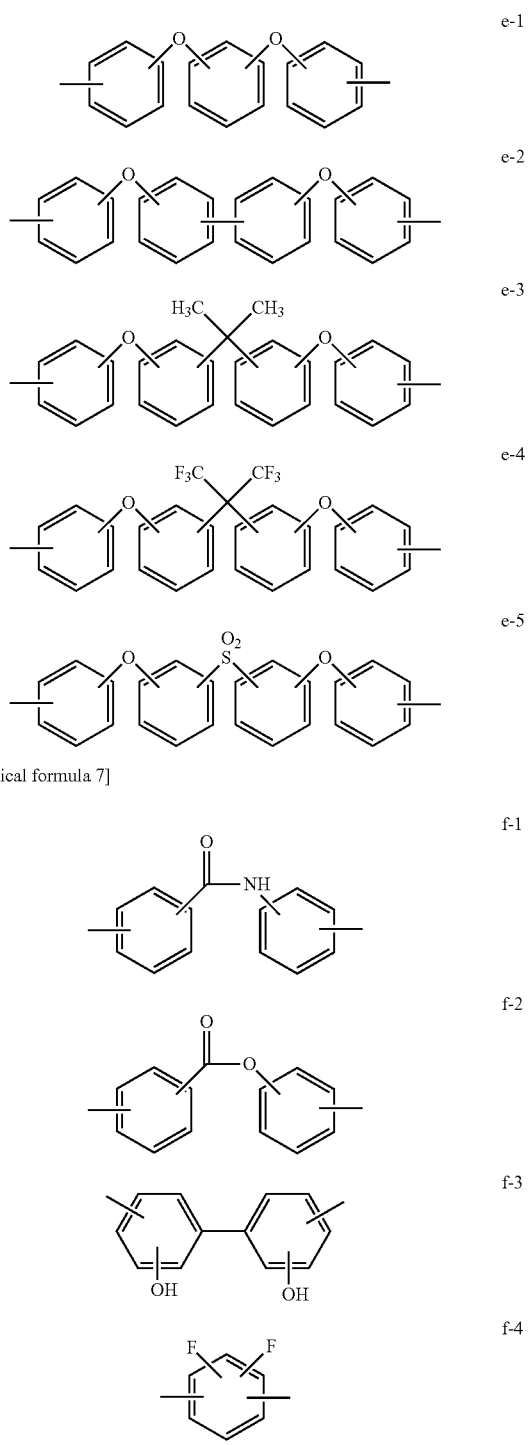

[Chemical formula 7]

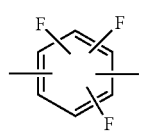
f-5

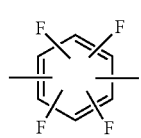
f-6

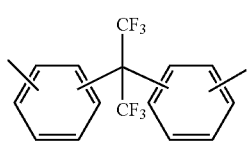
f-7

[Chemical formula 8]

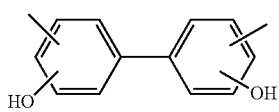
g-1

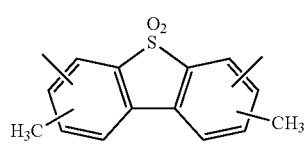
g-2

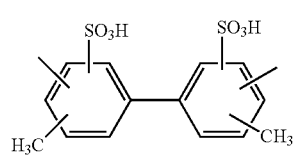
g-3

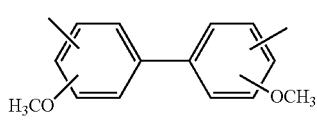
g-4

The divalent organic group having an aromatic ring as an example of Y may be, if substitution is allowed therefor, substituted with a group selected from the group consisting of a halogen atom (for example, fluorine atom, chlorine atom, bromine atom, or iodine atom, preferably fluorine atom or chlorine atom, and more preferably fluorine atom), a methyl group, and a trifluoromethyl group. Those substituent groups may be present in plurality, and, in that case, type of the substituent may be the same or different from each other. The suitable substituent for substitution on the divalent organic group having an aromatic ring is preferably a fluorine atom and/or a trifluoromethyl group when no fluorine atom is included in $X^0$, in particular, and it is more preferably a fluorine atom.

From the viewpoint of the property of forming a spheroid, Y in the above formula (I) is preferably a structure selected from the group consisting of d-3, d-9, e-1 to e-4, f-6, and f-7. It is more preferably a structure of e-1, e-3 or e-4, and even more preferably a structure of e-3.

In the above formula (I), $Z^1$, $Z^2$, $Z^3$, $Z^4$, $Z^5$, and $Z^6$ may be the same or different from each other, and, each independently, selected from a fluorine atom, a chlorine atom, a bromine atom, and an iodine atom, and in a case in which a fluorine atom is not included in at least one of $X^0$ and Y, at least one of $Z^1$, $Z^2$, $Z^3$, $Z^4$, $Z^5$, and $Z^6$ is preferably a fluorine atom.

From the viewpoint of the property of forming a spheroid, according to one preferred embodiment of the present invention, the divalent organic group represented by $X^0$ in the above formula (I) is preferably selected from the group consisting of —$C(CF_3)_2$— and above b-2 to b-10 and c-2 to c-10; and Y is selected from the group consisting of d-3, d-9, e-1 to e-4, f-6, and f-7. According to one more preferred embodiment of the present invention, the divalent organic group represented by $X^0$ in the above formula (I) is preferably selected from the group consisting of —$C(CF_3)_2$— and above b-7 to b-9 and c-7 to c-9; and Y is selected from the group consisting of d-e-1, e-3 and e-4.

The polyimide resin consisting of a constitutional unit represented by the above formula (I) can be obtained by a technique of calcining polyamide acid, which is obtained by polymerization between acid dianhydride and diamine. Hereinbelow, as one specific example, a process of synthesizing the 6FDA/BAPP copolymer is shown. Furthermore, the imidation rate of the "polyimide resin consisting of a constitutional unit represented by the formula (I)" is not necessarily 100%. Namely, the polyimide resin consisting of a constitutional unit represented by the formula (I) may consist only of a constitutional unit represented by the formula (I), but, within a range in which the effect desired in the present invention is not impaired, it is also acceptable that a constitutional unit in which the cyclic imide structure remains as amide acid with no dehydration ring-closure is included in part of the polyimide resin.

[Chemical formula 9]

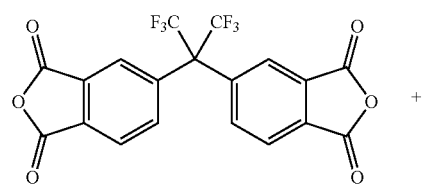
6FDA

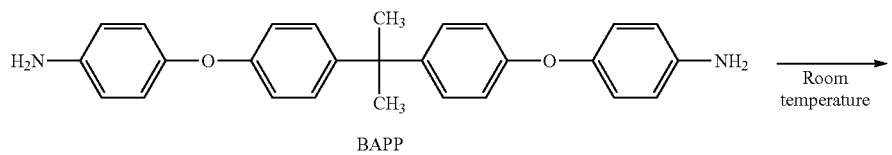
BAPP

Room temperature

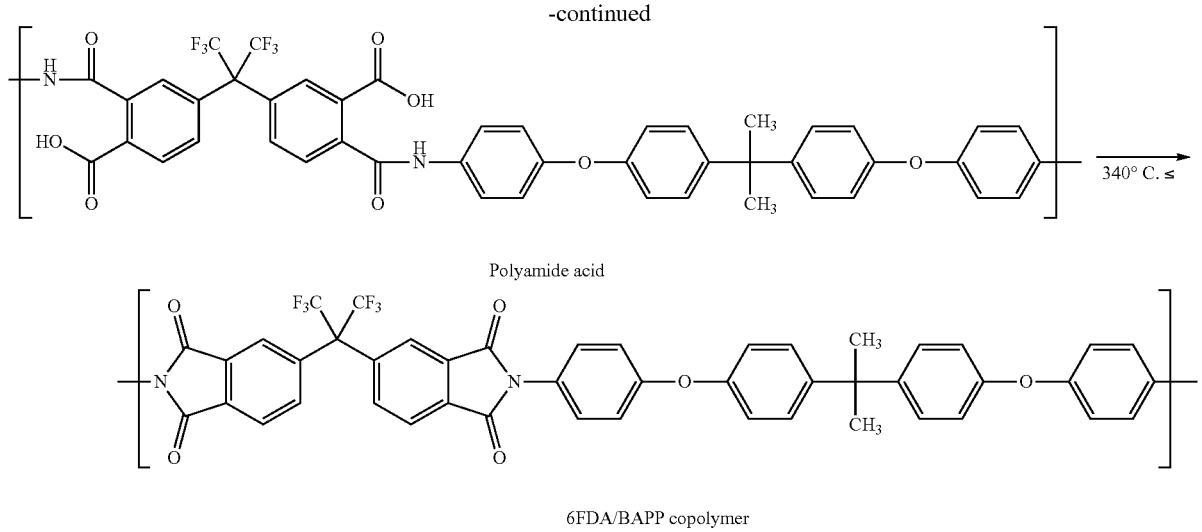

Polyamide acid

6FDA/BAPP copolymer

The reaction for synthesizing polyamide acid is suitably carried out in an organic solvent. As for the organic solvent used for the reaction for synthesizing polyamide acid, it is not particularly limited as long as it allows efficient progress of the reaction between acid dianhydride and diamine as a reaction material and is inert to those reaction materials. Examples of the organic solvent include a polar solvent such as N-methylpyrrolidone (NMP), N,N-dimethyl acetamide, N,N-dimethyl formamide, tetrahydrofuran, dimethyl sulfoxide, sulfolane, methyl isobutyl ketone, acetonitrile, benzonitrile, nitrobenzene, nitromethane, acetone, methyl ethyl ketone, isobutyl ketone, methanol, or the like; a non-polar solvent such as toluene, xylene, or the like; and the like. It is preferable to use a polar solvent among them. The organic solvent may be used either singly or as a mixture of two or more kinds thereof. The reaction mixture after amidation reaction may be directly subjected to thermal imidation. Concentration of the polyamide acid in the polyamide acid solution is not particularly limited. However, from the viewpoint of the polymerization reactivity and viscosity after polymerization of a resin composition to be obtained, film forming following thereafter, and easy handlability during calcining, the concentration is preferably 5% by weight or more, more preferably 10% by weight or more, and also, it is preferably 50% by weight or less, and more preferably 40% by weight or less.

According to imidation of the polyamide acid by any one of thermal imidation and chemical imidation, a resin composition including fluorine-containing polyimide is obtained. According to a specific embodiment, the polyamide acid is subjected to imidation by heating treatment (thermal imidation) to obtain a resin composition including fluorine-containing polyimide. Polyimide obtained by thermal imidation has almost no possibility of having residual catalyst and is more preferable for a use in cell culture. Furthermore, it is also acceptable that the imidation rate of the fluorine-containing polyimide resin is not 100%. Namely, the fluorine-containing polyimide resin may also contain, in part of the resin, a structural unit in which part of the cyclic imide structure of the structural unit that is represented by the above formula (I) has ring-opening to have an amide structure.

When the imidation is carried out by thermal imidation, by carrying out the imidation according to calcining of the polyamide acid at conditions under air, or more preferably in inert gas atmosphere like nitrogen, helium, argon, and the like, or in vacuum, preferably at temperature of 50 to 400° C., and more preferably 100 to 380° C., and preferably for 0.1 to 10 hours, and more preferably for 0.2 to 5 hours, the resin composition containing polyimide can be obtained.

The polyamide acid to be subjected to thermal imidation is preferably provided in the form in which the polyamide acid is dissolved in a suitable solvent. As for the solvent, it is sufficient to have those capable of dissolving the polyamide acid, and the solvent described above in relation to the reaction for synthesizing polyamide acid can be also used.

In the case of having the imidation by chemical imidation, the polyamide acid can be directly imidated, in a suitable solvent, by using a dehydrating cyclization reagent that is described later.

The dehydrating cyclization reagent can be used without any particular limitation as long as it has a function of chemical dehydrating cyclization of polyamide acid to yield polyimide. With regard to such dehydrating cyclization reagent, use of a tertiary amine compound alone or use of a tertiary amine compound and carboxylic acid anhydride in combination are preferable from the viewpoint of promoting the highly efficient imidation.

Examples of the tertiary amine compound include trimethylamine, triethylamine, tripropylamine, tributylamine, pyridine, 1,4-diazabicyclo[2.2.2]octane (DABCO), 1,8-diazabicyclo[5.4.0]undeca-7-ene, 1,5-diazabicyclo[4.3.0]nona-5-ene, N,N,N',N'-tetramethyl diaminomethane, N,N,N',N'-tetramethylethylene diamine, N,N,N',N'-tetramethyl-1,3-propane diamine, N,N,N',N'-tetramethyl-1,4-phenylene diamine, N,N,N',N'-tetramethyl-1,6-hexane diamine, N,N,N',N'-tetraethylmethylene diamine, N,N,N',N'-tetraethylethylene diamine, and the like. Among them, pyridine, DABCO, and N,N,N',N'-tetramethyl diaminomethane are preferable and DABCO is more preferable. The tertiary amine may be either only one kind or two or more kinds thereof.

Examples of the carboxylic acid anhydride include acetic anhydride, trifluoroacetic anhydride, propionic anhydride, butyric anhydride, isobutyric anhydride, succinic anhydride, maleic anhydride, and the like. Among them, acetic anhydride and trifluoroacetic anhydride are preferable, and acetic anhydride is more preferable. The carboxylic acid anhydride may be either only one kind or two or more kinds thereof.

As a solvent used for dissolving the polyamide acid in chemical imidation, a polar solvent having an excellent dissolution property is preferable. Examples thereof include tetrahydrofuran, N,N-dimethyl acetamide, N,N-dimethyl formamide, N-methylpyrrolidone, dimethyl sulfoxide, and the like. Among them, from the viewpoint of having a uniform reaction, it is preferable to have one or more kind selected from the group consisting of N,N-dimethyl acetamide, N,N-dimethyl formamide, and N-methylpyrrolidone. In a case in which those solvents are used as a solvent for the amidation reaction, it is also possible to use, without any separation from a reaction mixture after the amidation, directly the polyamide acid for chemical imidation.

Weight average molecular weight of the resin as a material for forming a base for cell culture is 5,000 to 2,000,000, for example. It is preferably 8,000 to 1,000,000 and more preferably 20,000 to 500,000. Furthermore, as described herein, the weight average molecular weight of a resin indicates a value that is measured by the following method. As the weight average molecular weight is within the above range, a more favorable spheroid forming property is obtained.

(Measurement of Weight Average Molecular Weight)

Apparatus: HCL-8220GPC manufactured by Tosoh Corporation

Column: TSKgel Super AWM-H

Eluent (NMP containing phosphate, LiBr.H$_2$O): 0.01 mol/L

Measurement method: 0.5% by weight solution is prepared with the eluent, and molecular weight is calculated based on a calibration curve which has been prepared with polystyrene.

Cell culture surface of a base for cell culture preferably has static water contact angle of 75° or more and sliding angle of 15° or more. When the base for cell culture satisfies such condition, forming of a spheroid on a base for cell culture is even further promoted. From the viewpoint of the property of forming a spheroid, the static water contact angle is more preferably more than 80°, and even more preferably more than 81°, and upper limit of the static water contact angle is less than 150°, for example, and it is preferably less than 120°, more preferably less than 100°, and even more preferably less than 90°. From the viewpoint of the property of forming a spheroid, it is preferable to have higher static sliding angle in the order of 18° or more, 20° or more, 22° or more, and 24° or more. Upper limit of the sliding angle is less than 80°, for example, and it is preferably less than 70°, more preferably less than 60°, and even more preferably less than 50°. Furthermore, the static water contact angle or sliding angle indicates a value that is measured by the following method.

(Method for Measuring Static Water Contact Angle)

Apparatus: Automatic contact angle meter (manufactured by Kyowa Interface Science Co., LTD.: DM-500)

Measurement method: Adhesion angle of liquid drop immediately after dropping 2 μL of water on a film is measured (measurement temperature: 25° C.)

(Method for Measuring Sliding Angle)

Apparatus: Automatic contact angle meter (manufactured by Kyowa Interface Science Co., LTD.: DM-500)

Measurement method: Base is continuously tilted after dropping 25 μL of water on a film, and the angle at the time of having falling-off is taken as the sliding angle (measurement temperature: 25° C.).

The base for cell culture may also include an additive component such as plasticizer, anti-oxidant, and the like. Thickness of the base is not particularly limited, either, and it can be arbitrarily set. It is 0.1 μm to 10 mm, for example, and preferably 1 μm to 1 mm.

The base for cell culture according to the present invention can be used for forming a spheroid even when it is not processed for forming a nano convex/concave structure. However, having a nano convex/concave structure is not excluded. The process for forming a nano convex/concave structure on a base for cell culture can be carried out by a technique described in JP 2014-210404 A, for example.

The base for cell culture may be also used in the form of a cell culture vessel. Specifically, the cell culture vessel of the present invention may be constituted such that the aforementioned base for cell culture is combined with other member (for example, supporting member), or it may be constituted such that the aforementioned base for cell culture is integrated with other member. The cell culture vessel may be constituted only with the aforementioned base for cell culture.

In a case in which the cell culture vessel is constituted such that the aforementioned base for cell culture is combined with other member, when a planar view of the vessel is obtained from an opening side of the cell culture vessel, internal shape and outer shape can have, each separately, any shape like circle, polygon (rectangle, triangle, or the like), and the like. Examples of a material constituting the supporting member include inorganic glass; carbon; metal such as silicon and the like; polyolefin resin such as polyethylene, polypropylene, cyclic olefin, and the like; polyester resin such as polyethylene terephthalate (PET) and the like; acrylic resin such as methyl polymethacrylate and the like; epoxy resin; polyvinyl chloride, polyvinylidene chloride, polystyrene resin, polyvinyl acetate, ABS (acrylonitrile-butadiene-styrene) resin, polycarbonate resin, vinyl ether, polyacetal, polyphenylene ether (PPE), polyaryl ether, polyphenylene sulfide (PPS), polyether ether ketone (PEEK), polyaryl ether ketone, phenol resin, polyether nitrile (PEN), and the like.

It is favorable for the cell culture vessel to have the aforementioned base for cell culture, and, as a whole, it can have any shape. For example, it can have a shape of various vessels such as plate for culture such as single, multi-well plate, or the like, petri dish, dish, flask, bag, or the like. Furthermore, the cell culture vessel may be in the form of a cell culture vessel for culture apparatus such as large-scale culture apparatus, perfusion culture apparatus, or the like.

<Use>

The disorder as a target of prophylaxis or treatment by the prophylactic or therapeutic agent of the present invention, which contains the aforementioned spheroid as an effective ingredient, is a cartilage tissue-related disorder.

The cartilage tissue-related disorder is a disorder related to cartilage tissues, and it means any disorder of which symptoms can be ameliorated by cartilage regeneration. Examples of the cartilage tissue-related disorder include arthrosis deformans of knee joint, traumatic cartilage injury, scapulohumeral periarthritis, temporomandibular joint disorder, joint rheumatoid arthritis, osteochondritis dissecans, aseptic osteonecrosis, medial meniscus injury, and the like.

As described above, a prophylactic or therapeutic agent for a cartilage tissue-related disorder containing, as an effective ingredient, the aforementioned spheroid is provided according to the present invention. However, from other point of view, the present invention also provides the followings.

A method for prophylaxis or treatment of a cartilage tissue-related disorder including administering a spheroid containing cultured mesenchymal stem cells to a patient in need thereof.

A spheroid containing cultured mesenchymal stem cells for use in prophylaxis or treatment of a cartilage tissue-related disorder.

Use of a spheroid containing cultured mesenchymal stem cells in the manufacture of a medicament for prophylaxis or treatment of a cartilage tissue-related disorder.

Although the mechanism by which the prophylactic or therapeutic agent containing, as an effective ingredient, the spheroid according to the present invention exhibits the aforementioned prophylactic or therapeutic effect against various cartilage tissue-related disorders is not entirely clear, the mechanism as follows is presumed.

Namely, as it is explained in the section of Examples to be described later, by containing cultured mesenchymal stem cells as an effective ingredient (preferably, by containing adherent cultured mesenchymal stem cells as an effective ingredient), the spheroid according, to the present invention is found to exhibit a significantly higher expression amount of TGFβ1 (Transforming Growth Factor (tumor growth factor)-β1) gene compared to a two-dimensional culture product.

Herein, TGFβ1 gene is a proliferation factor belonging to TGF-β super family, and there are isoforms of β1, β2, and β3 in mammalian TGF-β. TGFβ1 is responsible for, other than cell proliferation, the function like growth, differentiation, or control of mobility, and it is also known to be involved in physiological functions like embryo forming, tissue reconstruction, wound healing, and the like. Furthermore, human mature TGFβ1 has an amino acid sequence which has identity of 100% with pig, dog, and cow, or identity of 99% with mouse, rat, and horse, and also shows a crossover property. According to determination by the inventors of the present invention, it is believed that, as a result of showing a certain activity on regeneration or proliferation of cartilage tissues by an increased expression amount of the TGFβ1 gene, the prophylactic or therapeutic effect for a cartilage tissue-related disorder is exhibited.

Thus, the spheroid according to the present invention exhibits a significantly high expression amount of a certain gene compared to a two-dimensional culture product, but, with regard to the mechanism thereof, it is considered that, as a three-dimensional cell state is created by spheroid, a state close to the cell state found in living body is reproduced. It is also considered that, since the spheroid containing adherent cultured mesenchymal stem cells particularly follows a process that is close to the two-dimensional culture compared to a spheroid containing suspension cultured mesenchymal stem cells, as a result, the expression amount of gene is increased overall. Furthermore, because the spheroid containing adherent cultured mesenchymal stem cells is cultured in a state in which the spheroid is adhered onto a surface of a base for cell culture, there is less association among cells, and it consequently becomes possible to form a spheroid with relatively small size. Due to this reason, as there is less possibility of having blockage of nutrients or oxygen supply from a medium, the higher function (gene expression amount) can be exhibited.

The prophylactic or therapeutic agent according to the present invention can be prepared, stored, and administered in the same manner as before while making a reference to conventionally known cell preparations. The prophylactic or therapeutic agent according to the present invention has the form of an injection solution, in general. In the case of preparing an injection solution, after adding a pH adjusting agent, a buffering agent, a stabilizer, an isotonic agent, a local anesthetic, or the like to the effective ingredient, a subcutaneous, intramuscular, or intravenous injection solution can be produced by a common method. In that case, examples of the pH adjusting agent and buffering agent include sodium citrate, sodium acetate, sodium phosphate, physiological phosphate solution, and the like. Examples of the stabilizer include sodium pyrosulfite, ethylenediamine tetraacetic acid (EDTA), thioglycolic acid, thiolactic acid, and the like. Examples of the local anesthetics include procaine hydrochloride, lidocaine hydrochloride, and the like. Examples of the isotonic agent include sodium chloride, glucose, and the like.

If necessary, the prophylactic and/or therapeutic agent according to the present invention may further contain, in addition to the effective ingredient, various additive components that are generally used.

Amount of the effective ingredient to be contained in the prophylactic or therapeutic agent according to the present invention can be suitably set depending on dosage range of the effective ingredient, number of administration, or the like.

The dosage range is not particularly limited, and it can be suitably set depending on effectiveness of an ingredient to be contained, administration form, administration route, type of disorder, characteristics of a subject (bodyweight, age, symptoms, use of other pharmaceuticals, or the like), physician's opinion, or the like.

EXAMPLES

Effect of the present invention is explained by using the following Examples and Comparative Examples. However, the technical scope of the present invention is not limited to the following Examples. Furthermore, unless particularly described otherwise, the operations described below were carried out at room temperature (25° C.)

Production Example 1: Production of Fluorine-Containing Polyimide Film (Fluorine-Containing Polymer Base) (1)

To a three-neck flask with volume of 100 mL, 3.602 g (8.77 mmol) of 2,2-bis(4-(4-aminophenoxy)phenyl)propane (BAPP) and 42.5 g of N-methyl-2-pyrrolidone were added, and they were dissolved therein. To the mixture, 3.898 g (8.77 mmol) of 4,4'-hexafluoroisopropylidene diphthalic acid anhydride (6FDA) were added, and, by stirring for 5 days at room temperature under nitrogen atmosphere, a composition of fluorine-containing polyamide acid resin (solid content of 15.0% by mass) was obtained. Herein, weight average molecular weight of the obtained polyamide acid was 280,000. Furthermore, the weight average molecular weight of the polyamide acid and the weight average molecular weight of the fluorine-containing polyimide after calcination are substantially same as each other.

The composition of fluorine-containing polyamide acid resin as obtained above was applied on a glass substrate by using a die coater such that thickness of a fluorine-containing polyimide film after calcination was 40 μm, and thus a coating film was formed. Subsequently, calcination of the coating film was carried out for 1 hour at 340° C. under nitrogen atmosphere. After that, by releasing the calcined product from the glass substrate, fluorine-containing polyimide film 1 was obtained.

The fluorine-containing polyimide film 1 was found to have static water contact angle of 83.0° and sliding angle of 24.5°.

<Collecting Mesenchymal Stem Cells Derived from Adipose Tissues>

By using a known method employing collagenase treatment and centrifugal densitometry, stem cells derived from human adipose tissues (Adipose derived Stem Cell: AdSC) were collected from human adipose tissues.

Specifically, as a collagenase solution, collagenase type 1 (1 mg/mL, Wako Pure Chemical Corporation, 035-17604)/ 1% BSA HBSS solution containing DNaseI (0.1 mg/mL, Roche, 1284932) and 3 mM $CaCl_2$ was prepared first. Subsequently, human adipose tissues (1 g to 2 g or so) were finely minced using a mess, and, together with the above collagenase solution in a volume that is about 3 times the tissue volume, they were added to a 15 mL tube and subjected to shaking incubation for 60 minutes at 37° C. After that, to an inside of the incubated 15 mL tube, 5 mM EDTA/PBS (EDTA (0.5 M EDTA, pH 8.0, Life Technologies, AM9260G), prepared by dilution of 10×DPBS (Ca(−), Mg(−)) (GIBCO, 14200-166)) was added at room temperature to give a cell suspension of 15 mL or so followed by centrifuge treatment at 300×g for 5 minutes. After that, the supernatant (including lipid layer) was removed by suction, and then adjusted to 20 mL by adding 5 mM EDTA/PBS. The obtained cell suspension was passed through a cell strainer (70 μm, BD) and collected to a new 50 mL tube. To two 15 mL tubes added with 4 mL of Histopaque 1077 at room temperature, the cell solution as collected above was overlaid, 10 mL for each, without having any incorporation. The resultants were subjected to a centrifuge treatment at 800×g for 20 minutes (with no brake) at room temperature. After the centrifuge, only the monocyte cell layer was collected by a 2.5 mL syringe attached with 18 G needle, transferred to a new 15 mL tube, and adjusted to 14 mL with cold 5 mM EDTA/PBS. After that, the resultant was subjected to a centrifuge treatment at 200×g for 10 minutes (with brake) and the supernatant was discarded. Subsequently, the cells were suspended in 1 mL of cold 5 mM EDTA/PBS and messed up to 14 mL. They were then subjected to a centrifuge treatment at 200×g for 10 minutes, and the supernatant was discarded. The obtained cell pellet was suspended in a medium for primary cell culture (10% FBS/DMEM F12, SIGMA D8042+Antibiotic-Antimycotic, GIBCO 15240-062), and then sown on a petri dish at density of $3\times10^4/cm^2$ to $4\times10^4/cm^2$ or so. After that, the cells were cultured for 4 to 5 days in a 5% (v/v) $CO_2$ incubator, and the adherent cells were used for the following test as mesenchymal stem cells derived from human adipose tissues.

<Expansion Culture of Mesenchymal Stem Cells Derived from Human Adipose Tissues>

Mesenchymal stem cells derived from human adipose tissues as obtained from above were washed with 1 mL CELLOTION (manufactured by ZENOAQ) and adjusted to 10 mL by adding 10% FBS/DMEM F12 medium (manufactured by SIGMA). Subsequently, a centrifuge treatment at 250×g was carried out for 5 minutes. After the centrifuge treatment, the supernatant was removed, and, after suspension with 2 mL of 10% FBS/DMEM F12 medium (manufactured by SIGMA), cell number counting was carried out. The cell suspension was prepared so as to have concentration of $2\times10^5$ cells/mL. After that, 9 mL of medium was added in advance to a 100 mm dish (manufactured by FALCON), and 1 mL of the cell suspension which had been adjusted to the above concentration was added thereto. Then, in a 5% (v/v) $CO_2$ incubator at 37° C., expansion culture was carried out.

Example 1: Adherent Culture of Mesenchymal Stem Cells Derived from Human Adipose Tissues From the 100 mm dish, the medium was removed, and, after adding 3 mL of cell dissociating solution TrypLE select (manufactured by Thermo Fischer Scientific Inc.) thereto, the cells were maintained for 5 minutes in a 5% (v/v) $CO_2$ incubator at 37° C., and thus the cells were released. Subsequently, the resultant was transferred to a tube to have total amount of 10 mL by using 10% FBS/DMEM F12 medium. A centrifuge treatment at 250×g was carried out for 5 minutes, and, after suspension with 2 mL of 10% FBS/ DMEM F12 medium (manufactured by SIGMA), cell number counting was carried out. After that, preparation was made to have concentration of $1\times10^5$ cells/mL.

To a 24-well plate having a cell culture surface disposed with fluorine-containing polyimide film 1 as a fluorine-containing polymer base prepared in the above Production Example 1, the cell suspension prepared in the above was sown in an amount of 1 mL for each ($1\times10^5$ cells/well) (Day 0 of culture). After that, the culture was carried out in a 5% (v/v) $CO_2$ incubator at 37° C., and the culture was continued until Day 3.

As a result, it was confirmed by an observation using an optical microscope that, in accordance with a progress of the culture, a spheroid supported (adhered) on a fluorine-containing polymer base (fluorine-containing polyimide film 1) appeared. Herein, the observation image obtained by using an optical microscope is shown in FIG. 1. FIG. 1(a) shows the observation image on Day 1 of the culture, and FIG. 1(b) shows the observation image on Day 3 of the culture.

Example 2: Suspension Culture of Mesenchymal Stem Cells Derived from Human Adipose Tissues Except that PrimeSurface multi-well plate 24 well (manufactured by Sumitomo Bakelite Co., Ltd.) was used instead of the 24-well plate having a cell culture surface disposed with fluorine-containing polyimide film 1, culture of mesenchymal stem cells derived from human adipose tissues was carried out in the same method as the aforementioned Example 1.

Also in this Example, it was able to observe the formation of a spheroid. However, the spheroid was precipitated, in non-adherent state, on a bottom surface of the well without adhering onto a bottom surface of the well. Herein, the observation image on Day 3 of the culture, which was obtained by using an optical microscope, is shown in FIG. 2.

Comparative Example 1: Planar Culture of Mesenchymal Stem Cells Derived from Human Adipose Tissues Except that a 24-well polystyrene base (manufactured by FALCON) was used instead of the 24-well plate having a cell culture surface disposed with fluorine-containing polyimide film 1, culture of mesenchymal stem cells derived from human adipose tissues was carried out in the same method as the aforementioned Example 1. In this Comparative Example, the cultured cells only proliferated two-dimensionally (planar shape), and formation of a spheroid was not observed.

<Analysis of Gene Expression Amount>

From the culture plate in which culture of mesenchymal stem cells had been carried out in the Example 1, Example 2, and Comparative Example 1, cells were collected. From the collected cells, RNA was collected by using Nucleo Spin RNA (manufactured by COSMO BIO).

By using the collected RNA as a sample, expression amount of mRNA of human TGFβ1 gene (factor for causing cartilage differentiation) was measured by a quantitative PCR method. Furthermore, as a kit for quantitative PCR, BioRad SsoFast EvaGreen Mastermix (manufactured by Bio-Rad Laboratories, Inc.) was used, and the analysis was made by using the analyzing device BioRad CFXConnect 96 well (manufactured by Bio-Rad Laboratories, Inc.). The gene expression amount of TGFβ1 was calculated by correcting it as a relative value of the expression amount of each gene compared to an expression amount of GAPDH gene, which is a housekeeping gene. The results are shown in FIG. 3. FIG. 3 is a graph showing the result of the expression amount of human TGFβ1 gene under each culture condition.

As shown in the FIG. 3, in the Example 1 and Example 2, the mesenchymal stem cells cultured on fluorine-containing polyimide film 1 exhibited a significantly higher expression amount of human TGFβ1 gene compared to the cultured mesenchymal stem cells of the Comparative Example 1. Based on this result, it was found that expression of the gene is promoted in a spheroid containing cultured mesenchymal stem cells. Furthermore, from the comparison between the Example 1 and Example 2, it was also found that expression of the gene is more promoted in the adherent culture on a base for cell culture compared to the case of having suspension culture.

Production Example 2: Production of Fluorine-Containing Polyimide Film (Fluorine-Containing Polymer Base) (2)

To a three-neck flask with volume of 100 mL, 2.976 g (10.2 mmol) of 1,4-bis(aminophenoxy)bezene, 4.524 g (10.2 mmol) of 4,4'-hexafluoroisopropylidene diphthalic acid anhydride, and 42.5 g of N-methyl-2-pyrrolidone were added. According to stirring for 5 days at room temperature under nitrogen atmosphere, a composition of fluorine-containing polyamide acid resin (solid content of 15.0% by mass) was obtained. Herein, the weight average molecular weight of the obtained polyamide acid was 100,000. Furthermore, the weight average molecular weight of the polyamide acid and the weight average molecular weight of the fluorine-containing polyimide after calcination are substantially same as each other.

The composition of fluorine-containing polyamide acid resin as obtained above was applied on a glass substrate by using a die coater such that thickness of a fluorine-containing polyimide film after calcination was 40 μm, and thus a coating film was formed. Subsequently, calcination of the coating film was carried out for 1 hour at 360° C. under nitrogen atmosphere. After that, by releasing a calcined product from the glass substrate, fluorine-containing polyimide film 2 was obtained.

The fluorine-containing polyimide film 2 was found to have static water contact angle of 81.2° and sliding angle of 19.9°.

<Expansion Culture of Mesenchymal Stem Cells Derived from Human Adipose Tissues>

Mesenchymal stem cells derived from human adipose tissues as obtained from above were washed with 1 mL CELLOTION (manufactured by ZENOAQ) and adjusted to 10 mL by adding KBM ADSC-1 medium (manufactured by Kojin Bio Co., Ltd.). Subsequently, a centrifuge treatment at 250×g was carried out for 5 minutes. After the centrifuge treatment, the supernatant was removed, and, after suspension with 2 mL of KBM ADSC-1 medium (manufactured by Kojin Bio Co., Ltd.), cell number counting was carried out. The cell suspension was prepared so as to have concentration of $2 \times 10^5$ cells/mL. After that, 9 mL of medium was added in advance to a 100 mm dish (manufactured by FALCON), and 1 mL of the cell suspension which had been adjusted to the above concentration was added thereto. Then, in a 5% (v/v) $CO_2$ incubator at 37° C., expansion culture was carried out.

Example 3: Adherent Culture of Mesenchymal Stem Cells Derived from Human Adipose Tissues From the 100 mm dish, the medium was removed, and, after adding 3 mL of cell dissociating solution TrypLE select (manufactured by Thermo Fischer Scientific Inc.) thereto, the cells were maintained for 5 minutes in a 5% (v/v) $CO_2$ incubator at 37° C., and thus the cells were released. Subsequently, the resultant was transferred to a tube to have total amount of 10 mL by using KBM ADSC-2 medium (manufactured by Kojin Bio Co., Ltd.). A centrifuge treatment at 250×g was carried out for 5 minutes, and, after suspension with 2 mL of KBM ADSC-2 medium (manufactured by Kojin Bio Co., Ltd.), cell number counting was carried out. After that, preparation was made to have concentration of $1 \times 10^6$ cells/mL.

To a 35 mm petri dish having a cell culture surface disposed with fluorine-containing polyimide film 2 as a fluorine-containing polymer base prepared in the above Production Example 2, the cell suspension prepared in the above was sown in an amount of 0.2 mL for each ($2.0 \times 10^5$ cells/well) and added with 1.8 mL of KBM ADSC-2 medium (manufactured by Kojin Bio Co., Ltd.) (Day 0 of culture). After that, the culture was carried out in a 5% (v/v) $CO_2$ incubator at 37° C., and the culture was continued until Day 3.

As a result, it was confirmed by an observation using an optical microscope that, in accordance with a progress of the culture, a spheroid supported (adhered) on a fluorine-containing polymer base (fluorine-containing polyimide film 2) appeared.

Example 4: Suspension Culture of Mesenchymal Stem Cells Derived from Human Adipose Tissues ELPLASIA (manufactured by KURARAY CO., LTD.) was used instead of the 35 mm petri dish having a cell culture surface disposed with fluorine-containing polyimide film 2, which had been used in the Example 3. In addition, the cell suspension prepared to $3.5 \times 10^5$ cells/mL was sown, 1 mL for each (Day 0 of culture). After that, the culture was carried out in a 5% (v/v) $CO_2$ incubator at 37° C., and the culture was continued until Day 3. Furthermore, it was able to observe the formation of a spheroid also in this Example. However, the spheroid was precipitated, in non-adherent state, on a bottom surface of the well without adhering onto a bottom surface of the well.

Comparative Example 2: Planar Culture of Mesenchymal Stem Cells Derived from Human Adipose Tissues A 24-well polystyrene base (manufactured by FALCON) was used instead of the 35 mm petri dish having a cell culture surface disposed with fluorine-containing polyimide film 2, which had been used in the Example 3. In addition, the cell suspension prepared to 8×10³ cells/mL was sown, 1 mL for each (Day 0 of culture). After that, the culture was carried out in a 5% (v/v) $CO_2$ incubator at 37° C., and the culture was continued until Day 3. In this Comparative Example, the cultured cells only proliferated two-dimensionally (planar shape), and formation of a spheroid was not identified.

<Determination of Therapeutic Effect of Stem Cell Spheroid on Arthrosis Deformans of Knee Joint Using Model Mouse with Arthrosis Deformans of Knee Joint>

A 12-week old male BALE/c nude mouse was induced to have arthrosis deformans of knee joint (model with removed anterior cruciate ligament and semilunar valve). After preparing the model, sufficient exercise stress was applied thereto. One week later, the planar cultured mesenchymal stem cells obtained from the above Comparative Example 2 or a spheroid of the mesenchymal stem cells obtained from the above Example 4 and Example 5 were added to the joint (cartilage deficient area) of each mouse by intraarticular topical administration. Herein, the mesenchymal stem cells were added at 5×10⁴ cells/mouse, and also for the spheroid of mesenchymal stem cells, a spheroid consisting of 5×10⁴ cells was administered. At the time point of 3 weeks (Day 21) from the model preparation, autopsy was carried out and safranin O staining was performed to determine the thickness of cartilage layer of the head of tibia and staining state of cartilage base. The results are shown in FIG. 4 and FIG. 5. FIG. 4 is a graph showing the result of the semi-quantitative scoring evaluation of level of histological damage in joint in a model mouse with arthrosis deformans of knee joint, which has been administered with planar cultured mesenchymal stem cells obtained from the Comparative Example 2 or mesenchymal stem cell spheroid obtained from the Example 3 and Example 4 (lower score indicates less damage in joint). FIG. 5 is microscopic image showing the result of performing safranin O staining for joint tissues of a model mouse with arthrosis deformans of knee joint, which has been administered with planar cultured mesenchymal stem cells obtained from the Comparative Example 2 or a spheroid of the mesenchymal stem cells obtained from the Example 3 and Example 4 (lower score indicates less damage in joint).

As it is shown in the FIG. 4, the mouse administered with the spheroid obtained from the Example 3 and Example 4 exhibited an excellent result of scoring evaluation compared to the administration of planar cultured mesenchymal stem cells obtained from the Comparative Example 2. Furthermore, as it is shown in the FIG. 5, the mouse administered with the spheroid obtained from the Example 3 exhibited a thicker cartilage layer compared to the administration of the planar cultured mesenchymal stem cells obtained from the Comparative Example 2, and red color of the cartilage base stained by safranin O was also significantly higher (more favorable tendency was recognized compared to the Comparative Example 2). Furthermore, for the "blank" shown in the FIG. 4 and FIG. 5, the test was carried out similarly while administering only a buffer solution not containing any cells.

This application is based on Japanese Patent Application No. 2016-235286, filed Dec. 2, 2016, and Japanese Patent Application No. 2017-159670, filed Aug. 22, 2017, and their disclosures are incorporated herein in their entirety by reference.

The invention claimed is:

1. A prophylactic or therapeutic agent for treating a cartilage tissue-related disorder comprising an effective amount of a spheroid including mesenchymal stem cells obtained by adherent culture on a base for cell culture containing a polyimide resin in a blood serum-free medium.

2. The prophylactic or therapeutic agent according to claim 1, wherein the cartilage tissue-related disorder is selected from the group consisting of arthrosis deformans of knee joint, traumatic cartilage injury, scapulohumeral periarthritis, temporomandibular joint disorder, joint rheumatoid arthritis, osteochondritis dissecans, aseptic osteonecrosis, and medial meniscus injury.

3. The prophylactic or therapeutic agent according claim 1, wherein the mesenchymal stem cells are cells derived from human adipose tissues.

4. The prophylactic or therapeutic agent according to claim 1, wherein the polyimide resin is a fluorine-containing polyimide resin.

5. The prophylactic or therapeutic agent according to claim 1, wherein the prophylactic or therapeutic agent is administered by topical injection.

* * * * *